United States Patent [19]

Kijima et al.

[11] 3,998,858
[45] Dec. 21, 1976

[54] PROCESS FOR SYNTHESIS OF COENZYMES Q

[75] Inventors: Shizumasa Kijima; Isao Yamatu, both of Tokyo; Kimio Hamamura, Kashiwa; Norio Minami, Kawasaki; Youji Yamagishi; Yuichi Inai, both of Tokyo, all of Japan

[73] Assignee: Eisai Co., Ltd., Tokyo, Japan

[22] Filed: Dec. 12, 1975

[21] Appl. No.: 640,305

[52] U.S. Cl. .................. 260/396 R; 260/462 R
[51] Int. Cl.² .................................. C07C 49/73
[58] Field of Search .................. 260/396 R, 462 R

[56] References Cited
UNITED STATES PATENTS

| | | | |
|---|---|---|---|
| 3,549,668 | 12/1970 | Fukawa et al. | 260/396 R |
| 3,657,287 | 4/1972 | Kawamatsu et al. | 260/396 R |
| 3,896,153 | 7/1975 | Sato et al. | 260/396 R |

*Primary Examiner*—Vivian Garner
*Attorney, Agent, or Firm*—Woodhams, Blanchard and Flynn

[57] ABSTRACT 2,3-dimethoxy-5-methyl-6-substituted-1,4-benzoquinone having the formula:

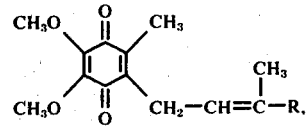

in which R is

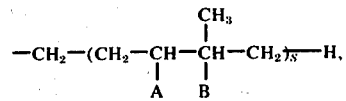

in which S is an integer of 0 to 11 and A and B stand for hydrogen or may form a direct bond, is prepared by reacting a boric acid ester of 2,3-dimethoxy-5-methyl-1,4-benzohydroquinone with prenol or isoprenol having the above group R and subsequently reacting the resulting borate with a mild oxidant. The compound is useful as coenzyme Q and has various clinical effects.

6 Claims, No Drawings

PROCESS FOR SYNTHESIS OF COENZYMES Q

BACKGROUND OF INVENTION

1. Field of Invention

This invention relates to a novel process for the synthesis of 2,3-dimethoxy-5-methyl-6-substituted-1,4-benzoquinones having the formula (I):

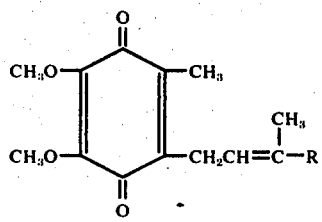

wherein R is a group of the formula

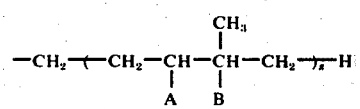

in which s is an integer of from 0 to 11, and A and B are hydrogen or A-B forms a direct bond.

Compounds of formula (I) are known as coenzymes Q, and especially, a compound of formula (I) in which A-B forms a direct bond and s is 9, namely 2,3-dimethoxy-5-methyl-6-decaprenyl-1,4-benzoquinone [2,3-dimethoxy-5-methyl-6-(3,7,11,15,19,23,27,31,35,39-decamethyl-tetracontadecaen-2,6,10,14,18,22,26,30,34,38,-yl)-1,4-benzoquinone], is called coenzyme $Q_{10}$ and is expected to show various clinical effects from the medicinal and pharmacological viewpoints because it participates in the electron transport system in living bodies and plays an important role in producing energies.

2. Description of Prior Arts

As the process for the synthesis of a series of quinone compounds represented by this coenzyme $Q_{10}$, there is known a process comprising reacting 2,3-dimethoxy-5-methyl-1,4-benzohydroquinone or its 1-monoacylate with (iso)decaprenol or its reactive derivative in the presence of an acidic condensation catalyst such as a protonic acid, e.g., formic acid, sulfuric acid, hydrochloric acid, phosphoric acid or p-toluenesulfonic acid, a Lewis acid, e.g., zinc chloride, aluminum chloride or a boron trifluoride-ether complex, or a mixture thereof, and if required hydrolyzing the condensation product, and oxidizing it to form the intended compound (see Japanese Pat. Publications No. 17513/64, No. 17514/64 and No. 3967/71).

In this known process, however, since the yield at the condensation step is not high, the yield of the intended quinone compound is 30% at the highest even when calculated as the crude product. Further, each of the acid catalysts used has a high corrosive property and has bad influences on equipment, and the metals dissolved out of the catalysts contaminate the products. Accordingly, this process is disadvantageous from the industrial viewpoint.

Moreover, since an acid catalyst as mentioned above should be used in the above known process, such operations as neutralization and extraction are required for separating the intended compound from the reaction mixture. Still further, a large quantity of the catalyst should naturally be used as compared with the amount of the starting reactants, and such catalyst should be discarded after completion of the reaction. Therefore, this known process is disadvantageous because the manufacturing cost is increased and the discarded catalyst causes environmental pollution. As is seen from the foregoing, this known process involves various industrial difficulties and disadvantages.

Various attempts have heretofore been made to improve the yield at the condensation step, and there has been developed a process in which 2,3-dimethoxy-5-methyl-6-halogeno-1,4-benzohydroquinone 1,4-dimethoxy-methyl ethers or 1,4-diacetates are linked with π-allyl type nickel complexes represented by the following chemical formula:

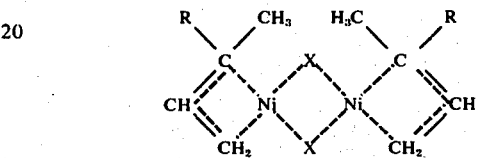

wherein x is halogen, R is as defined above, _____ denotes a semi-bond, and ___ denotes a double bond, and corresponding benzohydroquinones are obtained in high yields (see Japanese Patent Application Laid-Open Specifications No. 25137/72 and No. 85546/73). In this process, the yield at the condensation step can be highly improved, but since $Ni(CO)_4$ used for preparation of π-allyl type nickel complexes has a toxic activity to the respiratory organs and it is a gaseous substance and its handling is troublesome, it is very difficult to industrialize this process.

SUMMARY OF INVENTION

With a view to developing a process capable of providing quinone compounds at high efficiency, the inventors made research works for improving the condensation step so as to obtain industrially and effectively hydroquinone compounds, precursors of the intended quinone compounds. As a result, the inventors have now completed the process of the present invention.

More specifically, the synthesis process of the present invention comprises (a) reacting a boric acid ester of 2,3-dimethoxy-5-methyl-1,4-benzohydroquinone (II) with a prenol having the following formula:

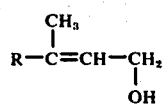

wherein R is as defined above, or an isoprenol having the following formula:

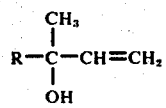

wherein R is as defined above, or its reactive derivative (III) to thereby form a boric acid ester of 2,3-dimethoxy-5-methyl-6-substituted-1,4-benzohydroquinone (IV) and (b) reacting the thus formed borate with a mild oxidant to thereby form a quinone compound represented by the formula (I), namely 2,3-dimethoxy-5-methyl-6-substituted-1,4-benzoquinone having the formula:

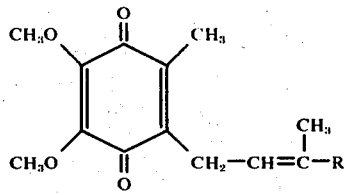

(I)

wherein R is as defined above.

In the step (a), the reaction (a) is carried out in the absence of a solvent or in the presence of at least one inert organic solvent such as benzene, toluene, xylene, n-hexane, cyclohexane, ethyl ether and tetrahydrofuran. Use of a solvent is generally advantageous because the reaction can be advanced smoothly and post treatments can be facilitated.

In practising the step (a), an organic solvent as mentioned above is used as the adsorption solvent, one of the compounds (II) and (III) is adsorbed in an adsorbent customarily used in chemical operations, such as silicic acid, silica gel, acid clay, kaolin, magnesium silicate (Florisil), active carbon, permutite, natural or synthetic zeolite, alumina, silica-alumina and silica-magnesia, and the other reactant, if desired in the state of being dissolved in the above organic solvent, is adsorbed and contacted according to a customary batch process or column process, whereby the reaction between both the reactants can be accomplished. The reaction product (IV) is extracted and desorbed from the adsorbent by using at least one organic solvent selected from, for example, ether type solvents such as ethyl ether, isopropyl ether, aromatic hydrocarbon solvents such as benzene, toluene and xylene, and aliphatic halogenated hydrocarbon solvents such as chloroform and trichloroethane.

The compound (II) used as the starting compound is prepared by reacting 2,3-dimethoxy-6-methyl-1,4-benzohydroquinone with boric acid according to the method disclosed in J. Am. Chem. Sec., 75 213 (1953), and formation of the compound (II) is confirmed by stretching in the adsorption at the B-O portion at 1385 cm$^{-1}$ in the infrared absorption spectrum. Since the compound (II) is very unstable to water and the like, it is desired that the compound (II) be synthesized every time it is required and the asprepared compound (II) be directly subjected to condensation with the compound (III) without isolation. As the prenol or isoprenol and its reactive derivative that can be used in the present invention, there can be mentioned, for example, 3-methylbutene-2-ol-1, 3-methylbutene-1-ol-3, geraniol, linalol, nerol, nerolidol, phytol, isophytol, geranylgeraniol, geranyllinalol, geranylfarnesol, geranylnerolidol, geranylgeranylfarnesol, solanesol, decaprenol, isodecaprenol, undecaprenol, dodecaprenol, and lower alkyl ethers, esters and halides of the foregoing alcohols.

According to this invention, boric acid can be used in all possible forms, including orthoboric acid ($H_3BO_3$), boron oxide ($B_2O_3$), metaboric acid ($HBO_2$), borax and so on. Among them, orthoboric acid is actually most preferred. When such boric acids are used in the reaction of this invention, borates (II) of 2,3-dimethoxy-6-methyl-1,4-benzohydroquinone are obtained, which are shown in their following possible structural formulas, as follows:

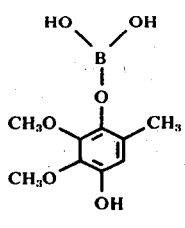

(V)

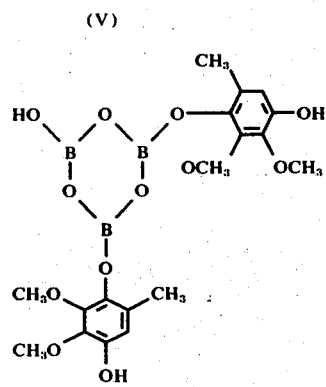

(VI)

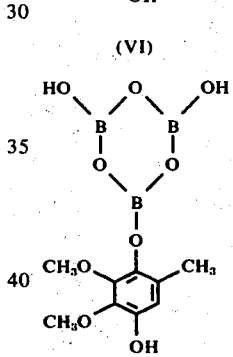

(VII)

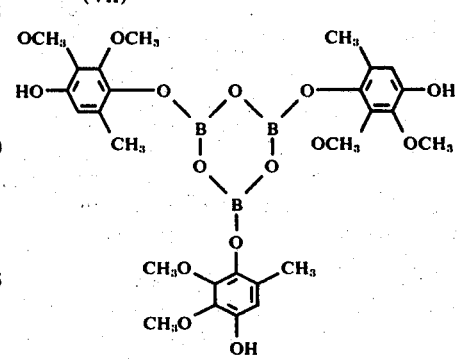

(VIII)

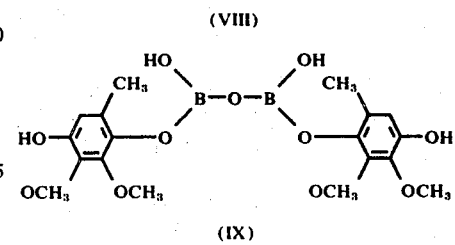

(IX)

-continued
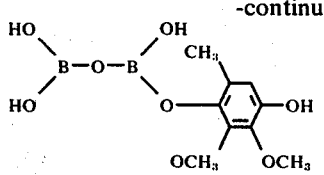
(X)
The compound (II) as mentioned above is first subjected to the reaction step (a) to obtain the borate (IV). The resulting compound (IV) is directly transferred to the subsequent step (b) without isolation and purification.
Typical possible structural formula of the compound (IV) follow:
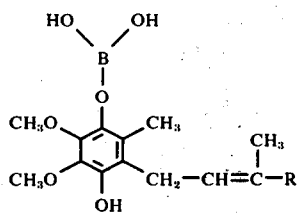
(XI)
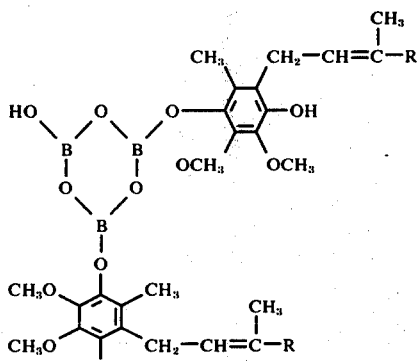
(XIII)
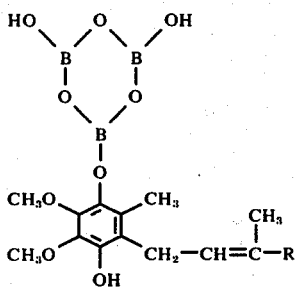
(XIII)
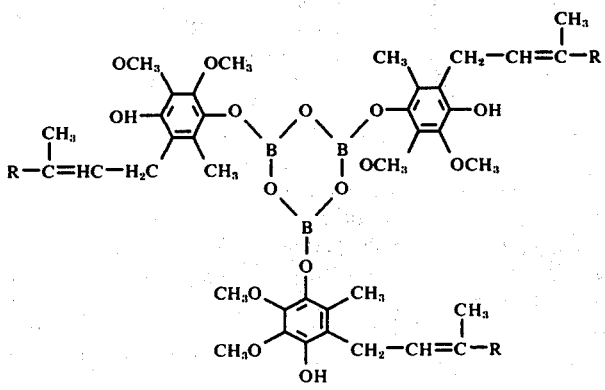
(XIV)

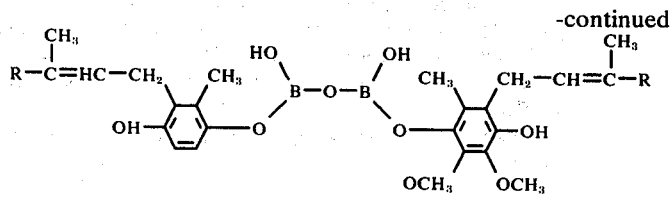

(XV)

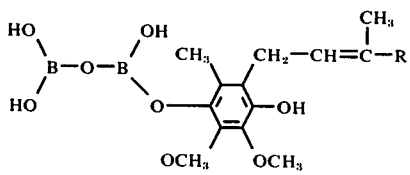

(XVI)

As the mild oxidant to be used at the second step (b), there can be mentioned, for example, silver oxide, lead oxide and ferric chloride disclosed in Japanese Pat. Publication No. 17514/64, and the like.

The process of the present invention makes the following improvements over the above-mentioned known processes:

1. Improvement of Yield:

In the process of the present invention, since the yield at the condensation step (a) is high, the intended final product (I) can be obtained in a high yield. For example, it was found that coenzyme $Q_{10}$ is prepared in a yield of 22% or higher when no adsorbent is used or in a yield of 45% or higher when an adsorbent is employed.

2. Decrease of Step Number:

The compound (IV) can be converted to the compound (I) directly without saponification. Accordingly, the saponification step can be omitted.

3. Other Effects:

There can be attained effects of preventing corrosion in equipments and the like and preventing environmental pollutions. In the conventional process, an acidic reagent such as zinc chloride, a boron trifluoride-ether complex or the like is used as a condensation catalyst at the step of condensing 2,3-dimethoxy-5-methyl-1,4-benzohydroquinone or its reactive derivative with an (iso)prenol or its reactive derivative. Since such acidic reagent has a high corrosive activity to a reaction vessel and other equipments, an anti-corrosive material should be used for the reaction vessel and the like. Further, when a metal halide is used as the catalyst, metal ions dissolved out from the catalyst cause environmental pollutions. In the present invention, since none of such acidic condensation catalysts are used, such disadvantages are not brought about at all.

As is apparent from the foregoing, the process of the present invention is highly improved over the conventional processes and is very excellent from the industrial viewpoint.

The present invention will now be illustrated in detail by reference to the following Examples.

EXAMPLE 1

Process for Synthesis of 2,3-Dimethoxy-5-Methyl-6-Decaprenyl-Benzoquinone-1,4

A mixture of 11 g of 2,3-dimethoxy-5-methylbenzohydroquinone-1,4 and 3.6 g of boric acid was heated in 50 ml of benzene. An azeotropic mixture formed was removed, and benzene was distilled off. To the residue was added 10 ml of toluene, and the mixture was heated at 50° to 55° C. and 14 g of decaprenol (having a purity of 90%) was added thereto under agitation. At the same temperature, agitation was continued for 5 hours. After completion of the reaction, the reaction mixture was extracted with 200 ml of ethyl ether, and the ether extract was washed with water, washed with aqueous alkali and dried with Glauber salt. Then, 6 g of silver oxide was added to the so treated ether extract, and the mixture was allowed to stand still overnight at room temperature under agitation. The reaction mixture was filtered, and the solvent was removed from the filtrate by distillation to obtain 15.9 g of an oily residue. The product was purified by silica gel chromatography using n-hexane containing 5% of ethyl ether as an elution solvent. The solvent was removed from the eluate by distillation to obtain 5.4 g of an orange-yellow oily substance. Crystallization from acetone gave 3.9 g (the yield being 22.6%) of an orange substance melting at 49° C.

The product was identified as the standard substance from the results of ultraviolet absorption spectrum analysis, infrared absorption spectrum analysis, nuclear magnetic resonance spectrum analysis and mass spectrum analysis.

EXAMPLE 2

Process for Synthesis of 2,3-Dimethoxy-5-Methyl-6-Decaprenyl-Benzoquinone-1,4

In toluene were refluxed 11 g of 2,3-dimethoxy-5-methyl-benzohydroquinone-1,4 and 3.6 g of boric acid, and after an azeotropic mixture formed had been removed, toluene was distilled off. To the residue were added 20 ml of benzene, 30 ml of hexane and 17 g of silica-alumina (N-633H manufactured by Nikki Kagaku), and a solution of 14 g of decaprenol (having a purity of 94%) in 10 ml of n-hexane was added dropwise over a period of 30 minutes to the mixture at 30° C. under agitation. At the same temperature, agitation was continued for 40 minutes. After completion of the reaction, the adsorbent was removed by filtration, and the resulting filtrate was concentrated and the concentrate was extracted with 300ml of ethyl ether. The ether extract was washed with water, washed with aqeuous alkali and dried with Glauber salt, and 6 g of silver oxide was added to the so treated ether extract. The mixture was allowed to stand still overnight at room temperature under agitation. The reaction mixture was filtered and the solvent was removed from the filtrate by distillation to obtain 16.3 g of an oily residue. The product was purified by silica gel chromatography using n-hexane containing 5% of ethyl ether as an elution solvent. The solvent was removed from the eluate by distillation to obtain 10.7 g of an orange-yellow oily substance. This substance gave a mono-spot in either thin layer or reverse layer chromatography.

The so obtained oily substance was crystallized from acetone to obtain an orange-yellow crystal melting at 49° C. The amount obtained of the product was 8.5 g (the yield being 49.2%).

As a result of the same measurements as mentioned in Example 1, the product was identified as the standard substance.

EXAMPLE 3

Process for Synthesis of
2,3-Dimethoxy-5-Methyl-6-Decaprenyl-Benzoquinone-1,4

In the same manner as described in Example 2, 11 g of 2,3-dimethoxy-5-methyl-benzohydroquinone-1,4, 3.6 g of boric acid and 14 g of decaprenol (having a purity of 94%) were reacted and treated, except that 20 g of Wako Gel C-200 (manufactured by Wako Junyaku) was used as an adsorbent and the condensation temperature was changed to 70° C.

There was obtained 7.7 g (the yield being 44.6%) of an orange-yellow crystal melting at 49° C.

As a result of the same measurements as described in Example 1, the product was identified as the standard substance.

EXAMPLE 4

Process for Synthesis of
2,3-Dimethoxy-5-Methyl-6-Nonaprenyl-Benzoquinone-1,4

In the same manner as described in Example 1, 11 g of 2,3-dimethoxy-5-methyl-benzohydroquinone-1,4, 3.6 g of borax and 12.6 g of solanesol were reacted and treated.

There was obtained an orange crystal melting at 45° C. The amount obtained of the product was 4.1 g (the yield being 25.8%).

As a result of the same measurements as described in Example 1, the product was identified as the standard substance.

EXAMPLE 5

Process for Synthesis of
2,3-Dimethoxy-5-Methyl-6-Phytyl-Benzoquinone-1,4

In the same manner as described in Example 2, 18 g of 2,3-dimethoxy-5-methyl-benzohydroquinone, 5.9 g of boric acid and 11 g of isophytol (having a purity of 90%) were reacted and treated.

There was obtained 13.3 g (the yield being 84.6%) of the intended product in the form of a red oily substance.

As a result of the same measurements as described in Example 1, the product was identified as the standard substance.

EXAMPLE 6

Process for Synthesis of
2,3-Dimethoxy-5-Methyl-6-Prenyl-Benzoquinone-1,4

In the same manner as described in Example 2, 18 g of 2,3-dimethoxy-5-methyl-benzohydroquinone-1,4, 5.6 g of boric acid and 6 g of 3-methylbutene-1-ol-3 were reacted and treated to obtain 12 g (the yield being 58.0%) of the intended product in the form of an oily substance of a dense red color.

As a result of the same measurements as described in Example 1, the product was identified as the standard substance.

EXAMPLE 7

Process for Synthesis of
2,3-Dimethoxy-5-Methyl-6-Decaprenyl-Benzoquinone-1,4

Eleven grams of 2,3-dimethoxy-5-methyl-benzohydroquinone-1,4, 2.1 g of boron oxide and 14 g of isodecaprenol having the purity of 90 percent were subjected to the same reaction as in Example 1 to obtain orange crystals having a melting point of 49° C. The yield was 21.4 percent (3.7 grams).

The product was identified as the standard substance from the results of ultraviolet absorption spectrum analysis, infrared absorption spectrum analysis, nuclear magnetic resonance spectrum analysis and mass spectrum analysis.

What is claimed is:

1. A process for the synthesis of 2,3-dimethoxy-5-methyl-6-substituted-1,4-benzoquinones having the formula:

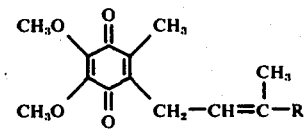

wherein R is a group of the formula:

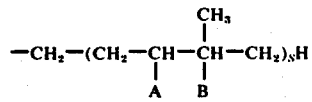

in which S is an integer of from 0 to 11, and A and B are hydrogen or A-B form a direct bond,
which comprises (a) reacting a boric acid ester of 2,3-dimethoxy-5-methyl-1,4-benzohydroquinone with a prenol having the formula:

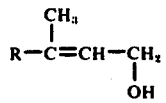

wherein R is as defined above, or an isoprenol having the formula:

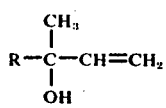

wherein R is as defined above or a reactive derivative thereof selected from the group consisting of lower alkyl ethers, esters and halides, to thereby form a boric acid ester of 2,3-dimethoxy-5-methyl-6-substituted-1,4-benzohydroquinone and (b) reacting the thus formed borate with a mild oxidant.

2. A process as claimed in claim 1, in which said boric acid ester is the orthoboric acid ester of 2,3-dimethoxy-5-methyl-1,4-benzohydroquinone.

3. A process as claimed in claim 1, in which said boric acid ester is the boron ester of 2,3-dimethoxy-5-methyl-1,4-benzohydroquinone.

4. A process as claimed in claim 1, in which said boric acid ester is the metaboric acid ester of 2,3-dimethoxy-5-methyl-1,4-benzohydroquinone.

5. A process as claimed in claim 1, in which said reactive derivative of prenol or isoprenol is selected from the group consisting of 3-methylbutene-2-ol-1,3-methylbutene-1-ol-3, geraniol, linalol, nerol, nerolidol, phytol, isophytol geranylgeraniol, geranyllinalol, geranylfarnesol, geranylnerolidol, geranyllinalol, geranylfarnesol, geranylnerolidol, geranylgeranylfarnesol, solanesol, decaprenol, isodecaprenol, undecaprenol, dodecaprenol, and lower alkyl ethers, esters and halides of the foregoing alcohols.

6. A process as claimed in claim 1, in which said mild oxidant is one or more oxidants selected from a group consisting of silver oxide, lead oxide and ferric chloride.

* * * * *

UNITED STATES PATENT AND TRADEMARK OFFICE
CERTIFICATE OF CORRECTION

PATENT NO. : 3 998 858
DATED : December 21, 1976
INVENTOR(S) : Shizumasa Kijima, Isao Yamatu, Kimio Hamamura, Norio Minami, Youji Yamagishi and Yuichi Inai It is certified that error appears in the above-identified patent and that said Letters Patent are hereby corrected as shown below:

Column 12, line 2; change "boron ester" to ---boron oxide ester---.

Signed and Sealed this

Tenth Day of May 1977

[SEAL]

Attest:

RUTH C. MASON
*Attesting Officer*

C. MARSHALL DANN
*Commissioner of Patents and Trademarks*